(12) United States Patent
Nakamura et al.

(10) Patent No.: US 6,617,168 B1
(45) Date of Patent: Sep. 9, 2003

(54) EVALUATION METHOD AND EVALUATION SYSTEM OF FREE HYPOHALOUS ACID CONCENTRATION

(75) Inventors: Shinichi Nakamura, Osaka (JP); Kunihiko Fukutsuka, Nabikino (JP); Yasushi Hanano, Osaka (JP)

(73) Assignee: Omega Co., Ltd., Osaka (JP)

( * ) Notice: Subject to any disclaimer, the term of this patent is extended or adjusted under 35 U.S.C. 154(b) by 0 days.

(21) Appl. No.: 09/226,377

(22) Filed: Jan. 6, 1999

(30) Foreign Application Priority Data

Jan. 8, 1998 (JP) ............................................. 10-002477

(51) Int. Cl.⁷ ............................................. G01N 33/00
(52) U.S. Cl. ........................... 436/125; 436/124; 436/2; 436/150; 204/410
(58) Field of Search .................. 436/124, 125, 436/164, 166, 169, 149, 150, 2; 422/56, 61; 205/778.5, 779, 779.5, 780, 403.15; 204/400

(56) References Cited

U.S. PATENT DOCUMENTS

| | | | | |
|---|---|---|---|---|
| 2,396,934 A | * | 3/1946 | Wallace ........................ 210/746 |
| 2,768,135 A | * | 10/1956 | Adelson ........................ 204/402 |
| 2,870,078 A | * | 1/1959 | Hood ............................ 204/400 |
| 3,669,857 A | * | 6/1972 | Kirkham et al. ............. 204/151 |
| 3,956,094 A | * | 5/1976 | Capuano ........................ 204/402 |
| 4,033,871 A | * | 7/1977 | Wall ............................. 210/96 |
| 4,073,873 A | * | 2/1978 | Caldwell et al. ............. 423/499 |
| 4,172,770 A | * | 10/1979 | Semersky et al. ........... 205/778 |
| 4,278,507 A | * | 7/1981 | Derreumaux et al. ....... 205/780 |
| 4,297,333 A | * | 10/1981 | Crawford et al. ........... 423/241 |
| 4,357,143 A | * | 11/1982 | Scott ........................... 205/778.5 |
| 4,400,304 A | * | 8/1983 | Clark et al. .................. 252/430 |
| 4,428,800 A | * | 1/1984 | Tarcy ............................ 204/1 T |
| 4,528,077 A | * | 7/1985 | Fair et al. ..................... 204/95 |
| 4,605,473 A | * | 8/1986 | Dewald ........................ 205/780 |
| 4,764,286 A | * | 8/1988 | Bon et al. ..................... 210/757 |
| 5,108,560 A | * | 4/1992 | Cawfield et al. ............. 204/103 |
| 6,024,850 A | * | 2/2000 | Sampson et al. ............ 204/296 |
| 6,030,842 A | * | 2/2000 | Peachey-Stoner et al. .. 436/125 |

FOREIGN PATENT DOCUMENTS

| | | | | |
|---|---|---|---|---|
| DE | 3701727 A1 | * | 8/1988 |
| JP | 355163452 A | * | 12/1980 |
| JP | 62245151 A | * | 10/1987 |
| JP | H3-235048 A | | 10/1991 |
| JP | 05245469 | * | 9/1993 |
| JP | 408094572 A | * | 4/1996 |
| JP | H9-15200 A | | 1/1997 |
| JP | 11023534 A | * | 1/1999 |

* cited by examiner

Primary Examiner—Jill Warden
Assistant Examiner—Yelena Gakh
(74) Attorney, Agent, or Firm—Koda & Androlia (57) ABSTRACT

The present invention provides an evaluation method and an evaluation system of free halogen concentration which eliminate the necessity of early exchanging or recycling of catalysts, as compared with a conventional method or system. In the present evaluation method of free halogen concentration, a main flow path of a sample liquid for evaluation and a sub-region that communicates with the main flow path are formed, a potential-measuring electrode is installed in the main path, while a reference electrode is installed in the sub-region at a position where free halogen in the sample liquid has been decomposed. Moreover, free halogen in the sample liquid is decomposed by a free-halogen decomposing substance in the sub-region, and the free halogen concentration is evaluated from the electric potential difference between the reference electrode and the potential-measuring electrode.

7 Claims, 11 Drawing Sheets

EVALUATION METHOD AND EVALUATION SYSTEM OF FREE HYPOHALOUS ACID CONCENTRATION

BACKGROUND OF THE INVENTION

1. Field of the Invention

The present invention relates to an evaluation method and an evaluation system of free halogen concentration.

2. Prior Art

The following means has been suggested in order to evaluate free halogen concentration (exhibiting a sterilizing effect) in various liquids.

A catalyst is placed in a flow path of a sample liquid for evaluation and the liquid is allowed to pass through it so that free halogen contained therein is decomposed. Further, a reference electrode is dipped and placed at a position at the downstream of the catalyst in the flow path. On the other hand, a potential-measuring electrode is dipped and placed at a position at the upstream of the catalyst in the flow path. Thus, the corresponding free halogen concentration is evaluated from the electric potential difference between the reference electrode and the potential-measuring electrode.

However, since, upon measurement, the sample liquid continues to pass through the catalyst, the activity of the catalyst is lowered with time. For this reason, conventional problems are that the consumed catalyst has to be exchanged by a new one in a short period and a recycling process has to be applied to the consumed catalyst by a heat treatment or other processes.

SUMMARY OF THE INVENTION

Therefore, it is an object of the present invention to provide an evaluation method and an evaluation system of free halogen concentration which eliminate the necessity of early exchanging or recycling of the catalyst, as compared with the conventional method and system.

In order to solve the above-mentioned problems, the present invention has the following technical means.

The evaluation method of free halogen concentration of the present invention is characterized in that: a main flow path of a sample liquid for evaluation and a sub-region which communicates with the main flow path are formed; a potential-measuring electrode is installed in the main path, while a reference electrode is installed in the sub-region at a position where free halogen of the sample liquid has been decomposed; free halogen in the sample liquid is decomposed by a free-halogen decomposing substance in the sub-region; and the free halogen concentration is evaluated from the electric potential difference between the reference electrode and the potential-measuring electrode. The sub-region can be described as a sub-flow path.

Moreover, the evaluation system of free halogen concentration of the present invention is characterized in that: with respect to the main flow path of the sample liquid and the sub-region which communicates with the main flow path, there are provided a potential-measuring electrode that is to be installed in the main flow path, a free-halogen decomposing substance for decomposing free halogen in the sample liquid in the sub-region and a reference electrode that is to be installed in the sub-region at a position where the free halogen in the sample liquid has been decomposed, whereby the free halogen concentration is evaluated from the difference in electric potential between the reference electrode and the potential-measuring electrode.

In the present invention, with respect to the main flow path of a sample liquid for evaluation and the sub-region which communicates with the main flow path, the potential-measuring electrode is installed in the main flow path and the reference electrode is installed in the sub-region at a position where the free halogen in the sample liquid has been decomposed.

Thus, upon measurement, the free halogen in the sample liquid is decomposed by the free-halogen decomposing substance in the sub-region, and the free halogen concentration is evaluated from the electric potential difference between the potential-measuring electrode and the reference electrode that is installed in the sub-region at the position where the free halogen in the sample liquid has been decomposed.

In this case, the free halogen in the sample liquid is allowed to be decomposed in the sub-region by the free-halogen decomposing substance in such a manner that the sample liquid is not allowed to pass through the free-halogen decomposing substance with time. That is, in contrast to a conventional system where the catalyst is installed in the flow path of a sample liquid for evaluation, the sample liquid is not allowed to pass through the free-halogen decomposing substance with time; therefore, the activity of the free-halogen decomposing substance is not susceptible to degradation with time.

For the above-mentioned free-halogen decomposing substance, a catalyst may be used; and activated carbon and oxides of nickel, iron, cobalt, titanium, manganese, etc. can be used as the catalyst. Further, a diaphragm, a salt bridge or a glass filter may also be used as the free-halogen decomposing substance.

An air-releasing means for discharging air and generated gases may be installed in the sub-region. With this arrangement, it is possible to avoid the possibility of the reference electrode being exposed out of the sample liquid by the presence of air and generated gases, and consequently to prevent the measurement of the electric potential difference from being interrupted.

DETAILED DESCRIPTION OF THE INVENTION

Hereinafter, preferred embodiments of the present invention will be described in detail with reference to the accompanying drawings.

Embodiment 1

Figure 1:
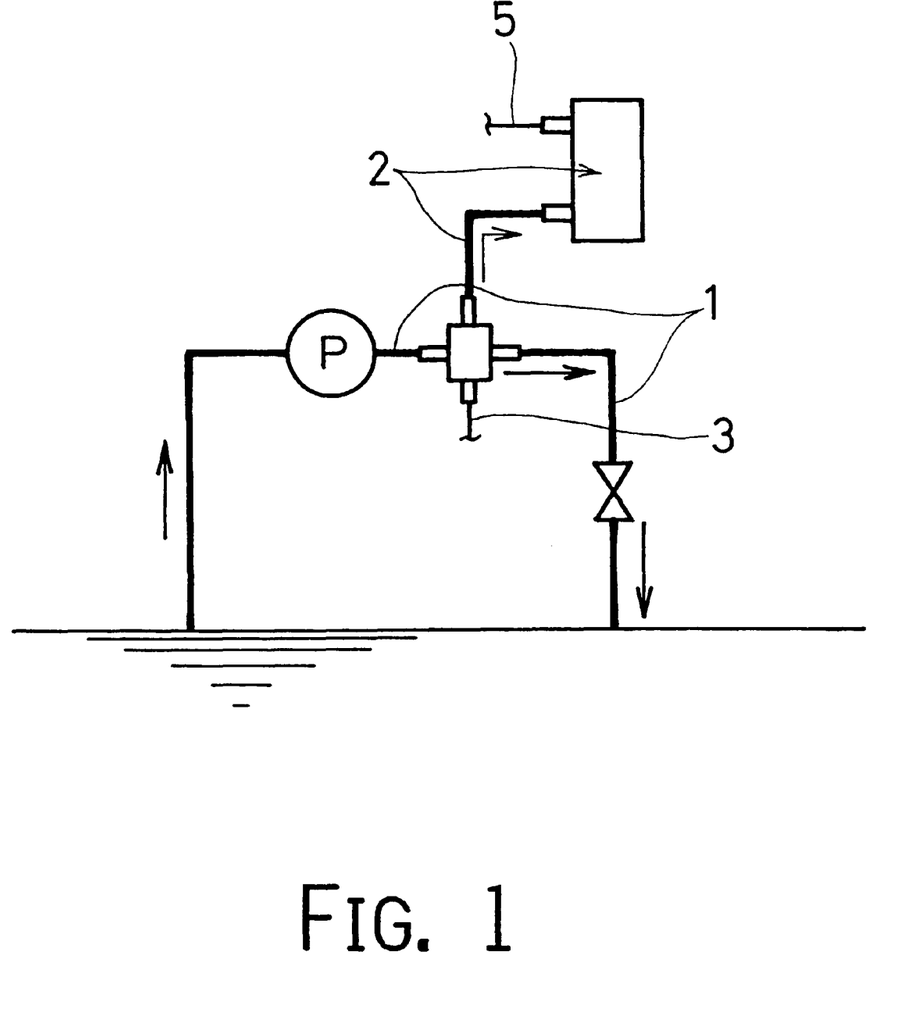
FIG. 1 is a drawing that schematically shows flow paths of Embodiment 1 of an evaluation system of free halogen concentration according to the present invention.
Figure 2:
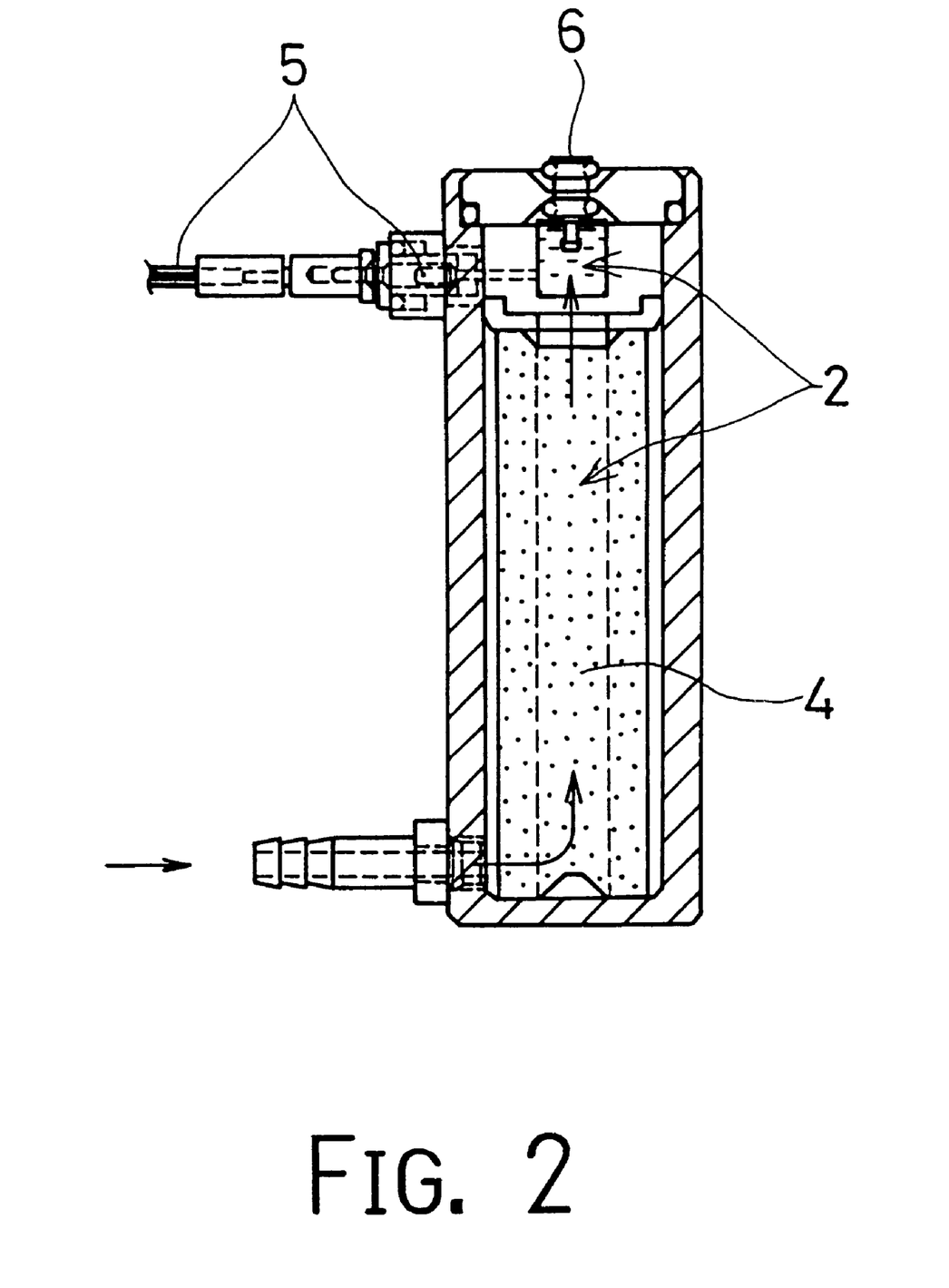
FIG. 2 is a cross-sectional view showing a structure of a casing including a reference electrode of Embodiment 1.
Figure 3:
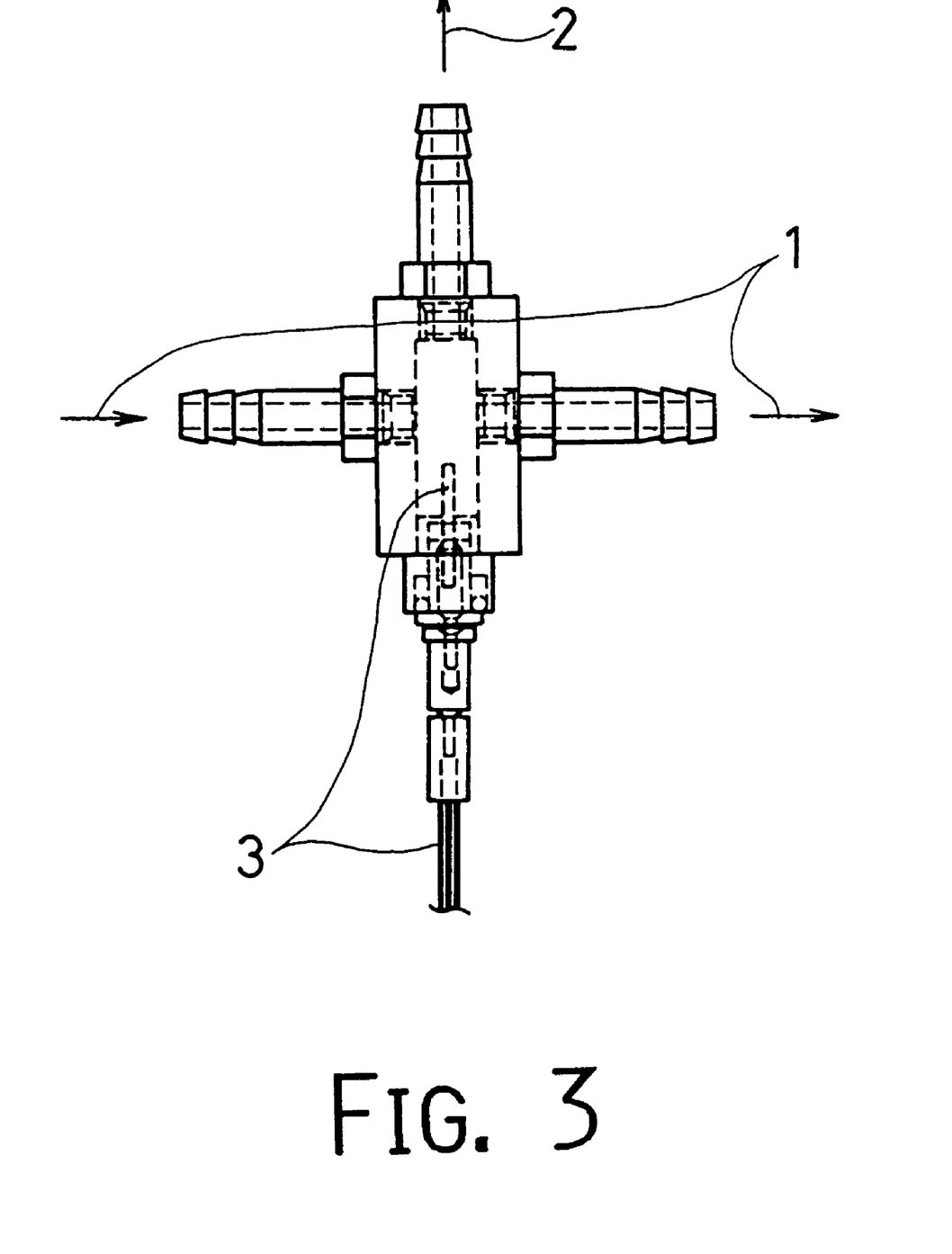
FIG. 3 is a cross-sectional view showing a structure of flow paths including a potential-measuring electrode of Embodiment 1.

As illustrated in FIGS. 1 through 3, the evaluation system of free halogen concentration of the present Embodiment is provided with a main flow path 1 through which a sample liquid for evaluation passes and a sub-region 2 (or "sub-flow path" as referred to in the above) communicating with the main flow path 1, and further provided with a potential-measuring electrode 3 that is to be installed in the main flow path 1, a free halogen decomposing substance 4 for decomposing free halogen in the sample liquid in the sub-region 2, and a reference electrode 5 that is to be installed at a position where the free halogen of the sample liquid has been decomposed in the sub-region 2, wherein the free halogen concentration is evaluated from the electric potential difference between the reference electrode 5 and the potential-measuring electrode 3.

A catalyst is used as the free halogen decomposing substrate 4, and the catalyst can be selected from the materials prepared as follows: fine particles or powder of activated carbon, an oxide of nickel, iron, cobalt, titanium, manganese, etc., ceramic, glass, igneous rock or other materials, is solely used, or some of them are used in mixed manner, and filled in a bag or a cassette which allows water to easily pass through. Moreover, instead of using the catalyst as the free halogen decomposing substance 4, a diaphragm (such as ion exchange membrane, etc.), salt bridge (such as potassium chloride solution, etc.), or a glass filter may be selected.

For the material of the potential-measuring electrode 3 and the reference electrode 5, materials such as platinum and gold that are corrosion resistant to the sample liquid are preferably used.

An automatic air-releasing valve for discharging air and generated gases is installed in the sub-region 2 as an air-releasing means 6. The air-releasing means 6 prevents the reference electrode 5 from being exposed out of the sample liquid in which free halogen has been decomposed due to the presence of air and generated gases, thereby preventing the measurement of the electric potential difference from being interrupted.

In this evaluation method of free halogen concentration, the main flow path 1 for a sample liquid for evaluation and the sub-region 2 communicating with the main flow path 1 are formed, the potential-measuring electrode 3 is installed in the main flow path 1, the reference electrode 5 is installed at a position where the free halogen of the sample liquid has been decomposed in the sub-region 2, the free halogen in the sample liquid is decomposed by the free halogen decomposing substance 4 in the sub-region 2, and the free halogen concentration is evaluated from the electric potential difference between the reference electrode 5 and the potential-measuring electrode 3.

Next, an explanation will be given of a state in which the present Embodiment is used.

First, with respect to the main flow path 1 for a sample liquid for evaluation and the sub-region 2 communicating with the main flow path 1, the potential-measuring electrode 3 is installed in the main flow path 1, and the reference electrode 5 is installed at a position where the free halogen of the sample liquid has been decomposed in the sub-region 2.

Upon measurement, the free halogen in the sample liquid is decomposed by the free halogen decomposing substance 4 in the sub-region 2, and the free halogen concentration is evaluated from the electric potential difference between the reference electrode 5 and the potential-measuring electrode 3 placed at the position where the free halogen in the sample liquid has been decomposed in the sub-region 2.

That is, the free halogen is decomposed by the catalyst serving as the free halogen decomposing substance 4 in the sub-region 2; and since halogen ions ($Br^-$, $Cl^-$, etc.) exist, an electric current flows between the reference electrode 5 and the potential-remeasuring electrode 3, thereby making it possible to measure an electric potential difference between those electrodes. Moreover, because of the presence of the conductive sample liquid between the reference electrode 5 and the potential-measuring electrode 3, the electric potential difference can be measured between the two electrodes.

Here, the free halogen in the sample liquid is decomposed by the free halogen decomposing substance 4 in the sub-region 2 so that the sample liquid is not allowed to pass through the free halogen decomposing substance 4 with time. Therefore, it is difficult to lower the activity of the free halogen decomposing substance 4 with time, thereby eliminating the necessity of early exchanging or recycling of the catalyst as required in the conventional system.

Embodiment 2

Next, an explanation will be given of Embodiment 2 while making a comparison with Embodiment 1.

Figure 4:
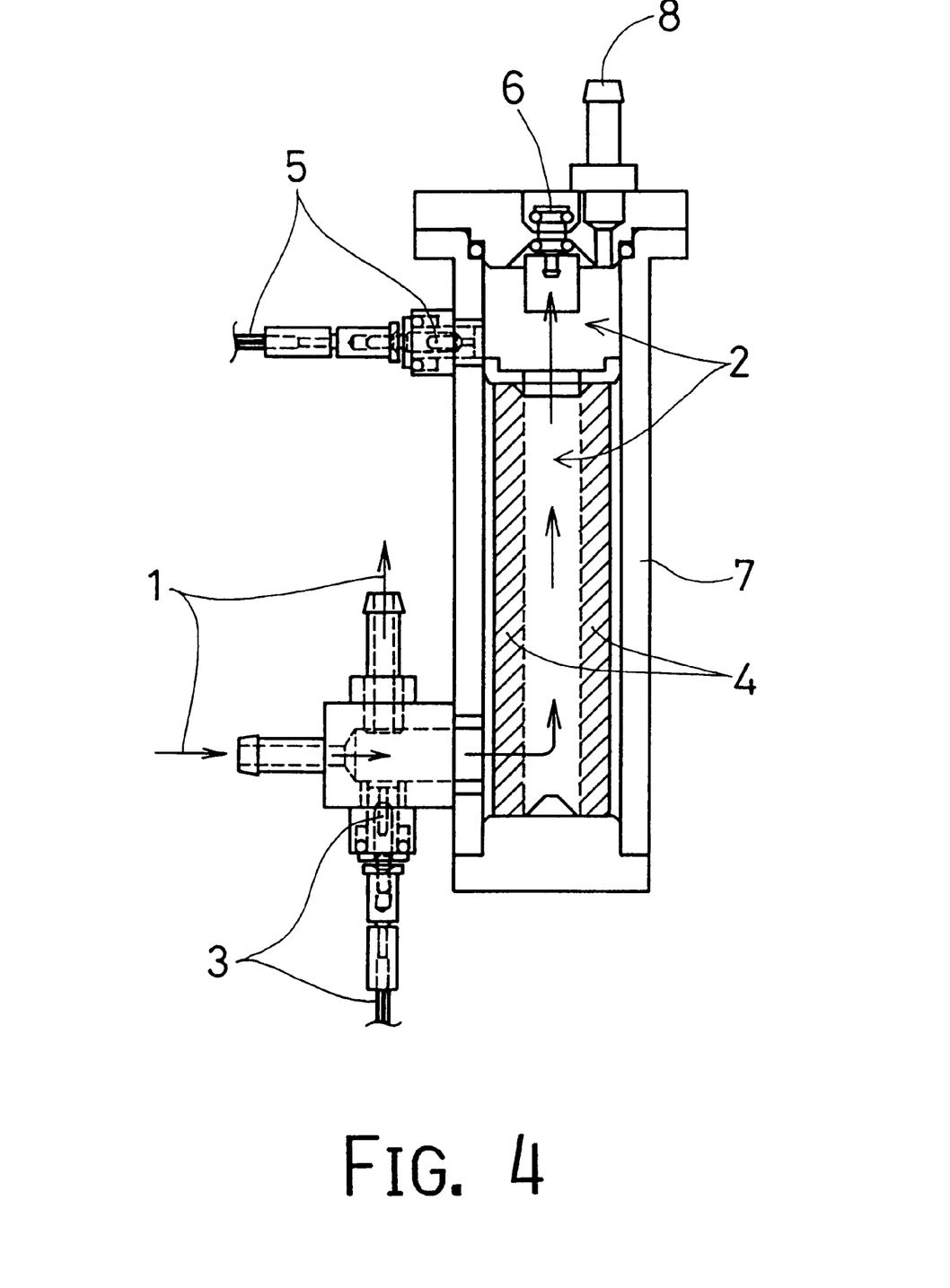
FIG. 4 is a cross-sectional view showing an internal structure of a casing of Embodiment 2 of the evaluation system of free halogen concentration according to the present invention.
Figure 5:
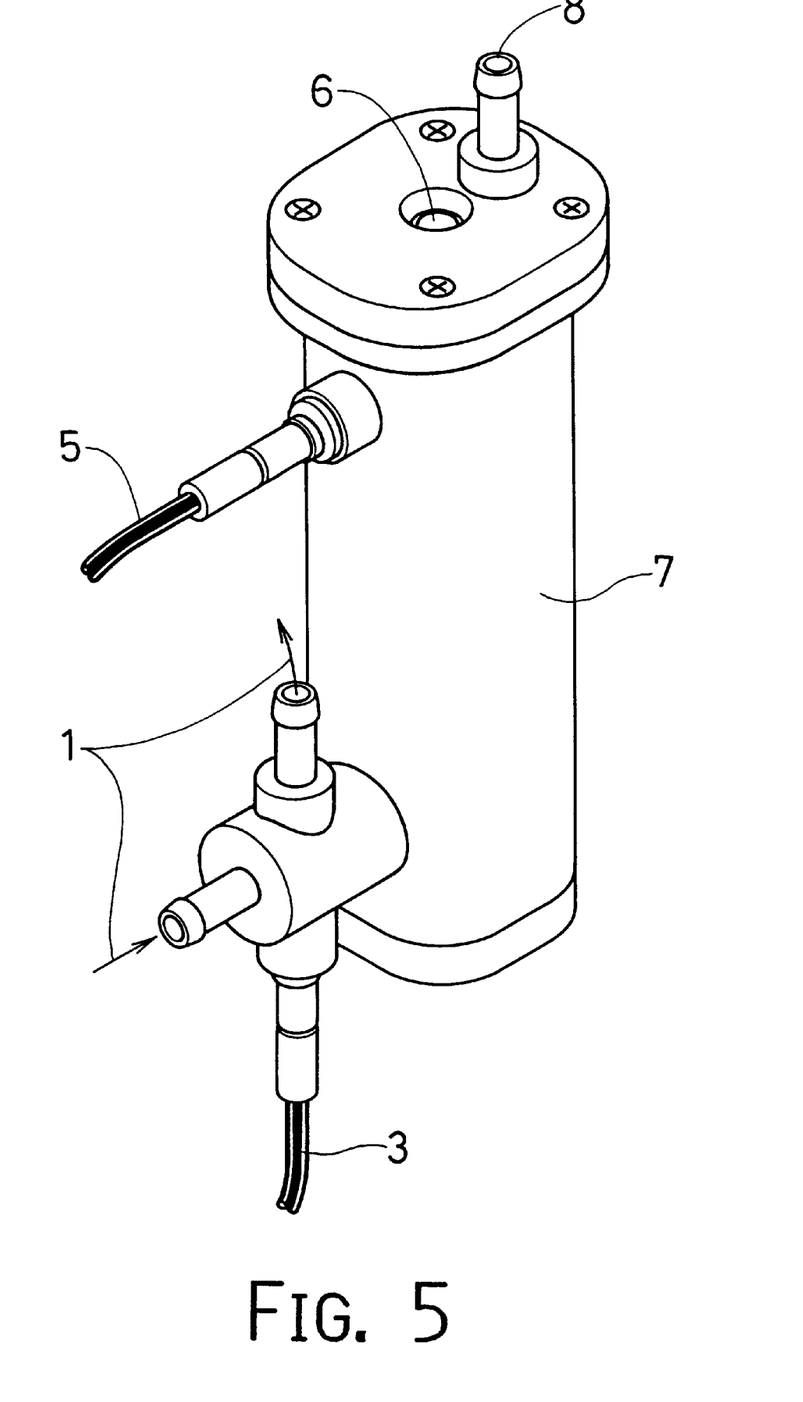
FIG. 5 is a perspective view showing the entire structure of the casing of Embodiment 2.

As illustrated in FIG. 4 and FIG. 5, a reference electrode 5, a potential-measuring electrode 3, and a catalyst (4) are integrally formed in a casing 7 in this Embodiment, in order to provide a compact structure to the portion related to measurements of the electric-potential difference in the sample liquid for evaluation in the evaluation system of free halogen concentration. Here, an activated carbon filter having a hollow cylinder shape made by molding fiber which is preliminarily interweaved with activated carbon is used as the catalyst (4).

An automatic air-releasing valve of a float type is used as an air-releasing means 6; thus, air and gases (hydrogen, oxygen, chlorine, etc.) generated from the sample liquid are automatically released.

Moreover, an overflow nozzle 8 is a nozzle used for allowing some of the sample liquid that has flowed thereto to overflow, in order to remove air from the sub-region 2 upon initially using this system. Once this overflowing process is carried out, air is released, and it is not necessary to exchange the liquid in this portion every time the sample liquid is changed.

Embodiment 3

Next, an explanation will be given of Embodiment 3 while making a comparison with the above-mentioned Embodiment.

Figure 6:
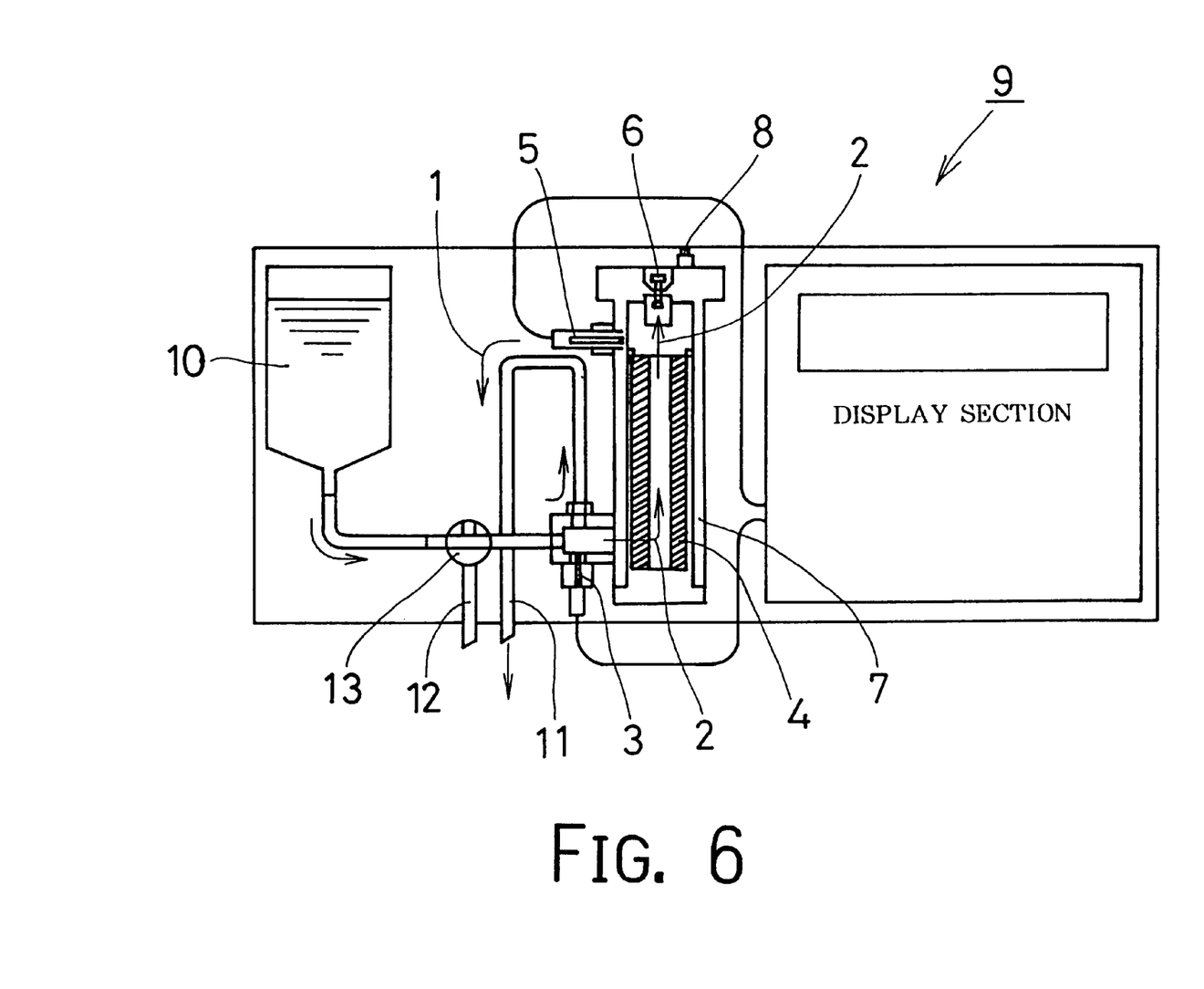
FIG. 6 is a drawing showing a structure of a free halogen concentration evaluating device of Embodiment 3 of the evaluation system of halogen concentration according to the present invention.

As illustrated in FIG. 6, in this Embodiment, a free halogen concentration evaluating device 9 is formed by combining the evaluation system of free halogen concentration into one unit.

This construction is formed by utilizing the portion related to measurements on the electric potential difference of the sample liquid as shown in Embodiment 2 (see FIG. 4 and FIG. 5), and by being further provided with other components such as a vessel 10 which supplies a sample liquid for evaluation and piping flow paths from the vessel. Further, a well-known electric potential difference conversion amplifier circuit, used for detecting an electric potential difference, is built therein, and a display section for the electric potential difference and the evaluated concentration of free halogen is installed. Such a compact construction allows for a portable use.

With respect to the catalyst (4), a fibrous activated carbon filter into which coconut shell activated carbon is interwoven by a binder (manufactured by Kuraray Co., Ltd.) was used.

Here, reference numeral 11 represents a discharging pipe for the sample liquid, 12 represents a drain pipe for liquid for inspection, and 13 is a three-way cock for discharging the sample liquid in the vessel after completion of the measurement.

Embodiment 4

Next, an explanation will be given of Embodiment 4 while making a comparison with the above-mentioned Embodiments.

Figure 7:
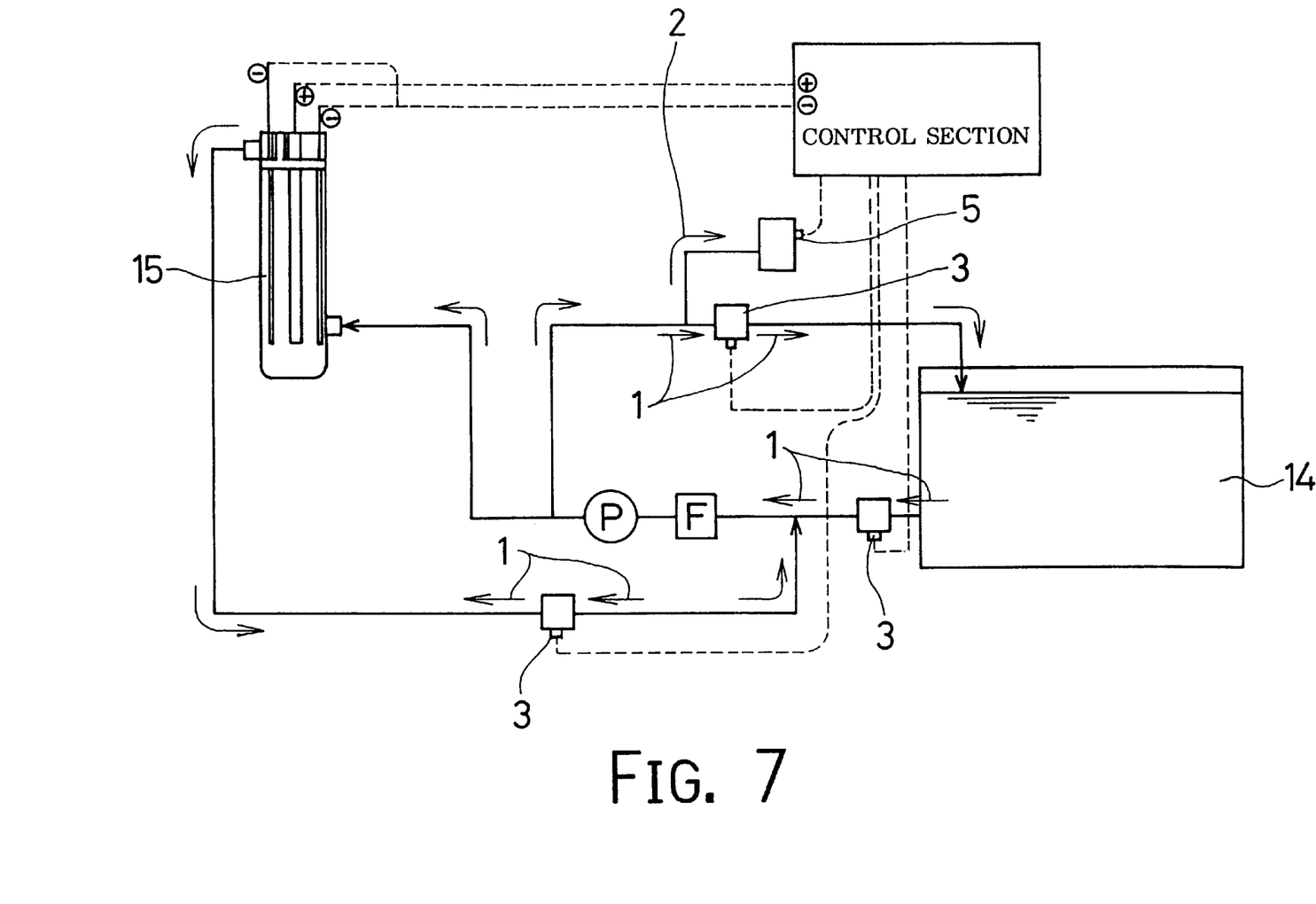
FIG. 7 is a drawing showing a circulating flow path of a water-purifying sterilization system of Embodiment 4 to which the evaluation system of free halogen concentration of the present invention is applied.
Figure 8:
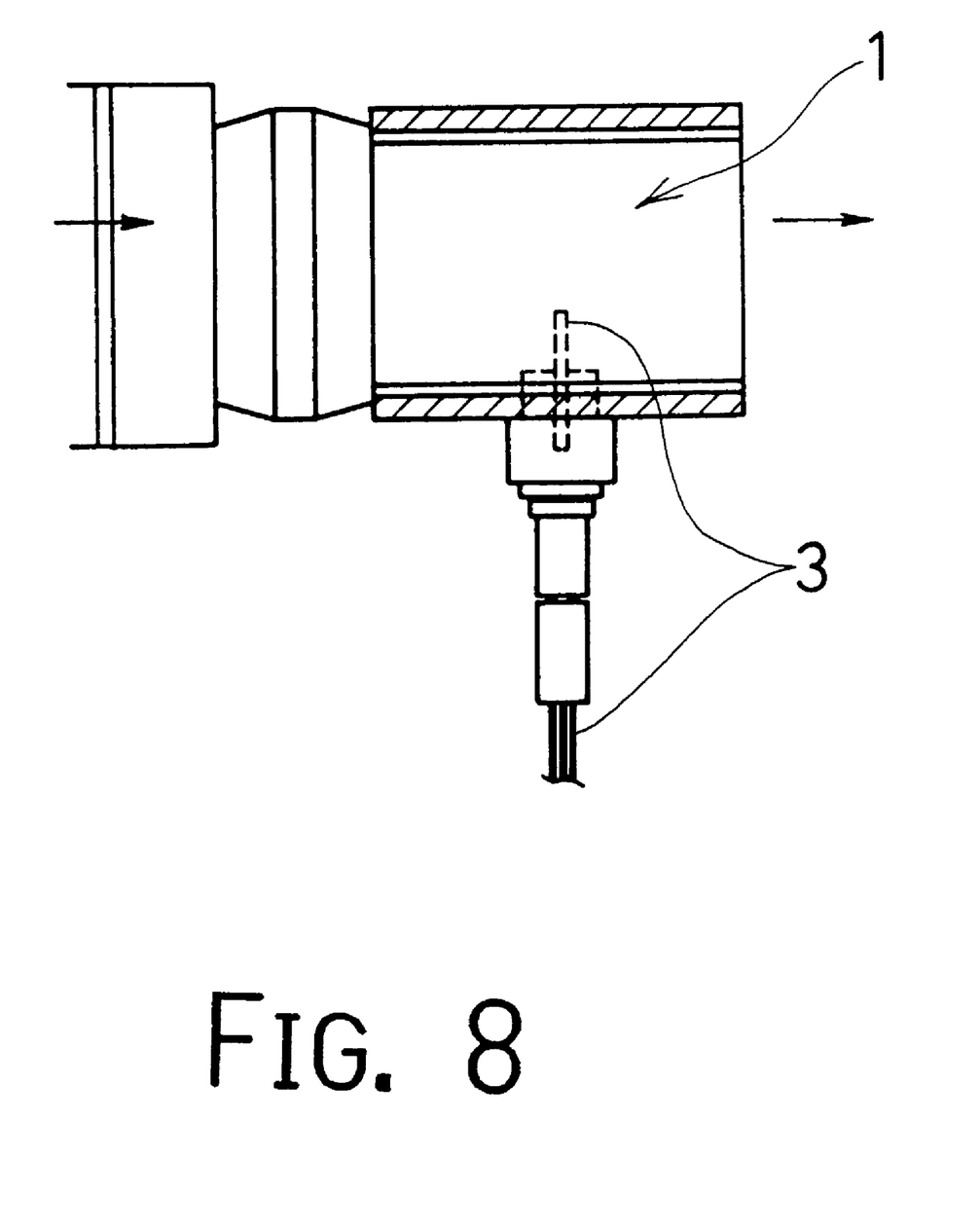
FIG. 8 is a cross-sectional view showing a structure of a potential-measuring electrode of Embodiment 4.

As illustrated in FIG. 7 and FIG. 8, in this Embodiment, the evaluation system of free halogen concentration is applied into a circulating flow path of a water-purifying sterilization system for a sample water.

This water-purifying sterilization system has an arrangement in which water in a sample water vessel 14 is supplied into an electrolytic system through a circulating flow path so as to be purified and sterilized by electrolysis, and then again returned to the sample water vessel 14. As for the sample water vessel 14, for example, a bathtub of a 24-hour (around-the-clock) bath system is listed.

As illustrated in FIG. 8, the potential-measuring electrode 3 has a construction in which an electrode is attached to a short tube with a flange, and one reference electrode 5 and three potential-measuring electrodes 3 are installed in the circulating flow path between the sample water vessel 14 and the electrolytic system 15.

Here, in the water-purifying sterilization system of the sample water vessel 14, it is sometimes necessary to evaluate the free halogen concentration at a plurality of portions in the circulating path; and by using a plurality of potential-measuring electrodes 3 (three in this Embodiment) that are placed in the circulating flow path as described above and evaluating the free halogen concentration successively at those portions while switchovers are made on a control circuit, the electrolysis of the water-purifying sterilization system can be preferably controlled based upon the evaluated concentrations.

Next, a more specific construction of the present invention will be described below.

Example 1

By using the free halogen concentration evaluating device 9 (see FIG. 6) of Embodiment 3, the correlation between the measured value of the electric potential difference and the actual free halogen concentration was confirmed in the following method.

Sample liquid was prepared through electrolysis, and this was diluted so as to obtain solutions having different concentrations. The free halogen concentration of the electrolyzed sodium bromide solution was 30 ppm (measured by a conventional concentration-measuring device), and the free halogen concentration of the electrolyzed salt water was 32 ppm (measured by a conventional concentration-measuring device).

Pure water was added to the electrolyzed salt water having 32 ppm so as to dilute it to 10 ppm (measured by a conventional concentration-measuring device), and evaluation was started. The sample liquid was stored in the vessel 10, and at the time when 5 to 10 cc of it had been discharged from the discharging pipe for the sample liquid, the electric potential-difference amplifier circuit was driven and the display of the electric potential difference was checked.

Successively, pure water was further added to the salt water for inspection having 10 ppm so as to dilute it to 7 ppm (adjusted by a conventional concentration-measuring device), and evaluation was made on the electric potential difference in the same manner as the sample of 10 ppm concentration. Thereafter, the same evaluation processes were repeated until the sample of 0.5 ppm concentration was evaluated (adjusted by a conventional concentration-measuring device). Next, the sample of 30 ppm concentration (adjusted by a conventional concentration-measuring device) was evaluated, and then diluting and evaluating were repeated in the same manner until the sample of 12 ppm concentration was evaluated (adjusted by a conventional concentration-measuring device).

The evaluation of the electric potential difference was done on the sodium bromide solution in the same manner as on the salt water.

Figure 9:
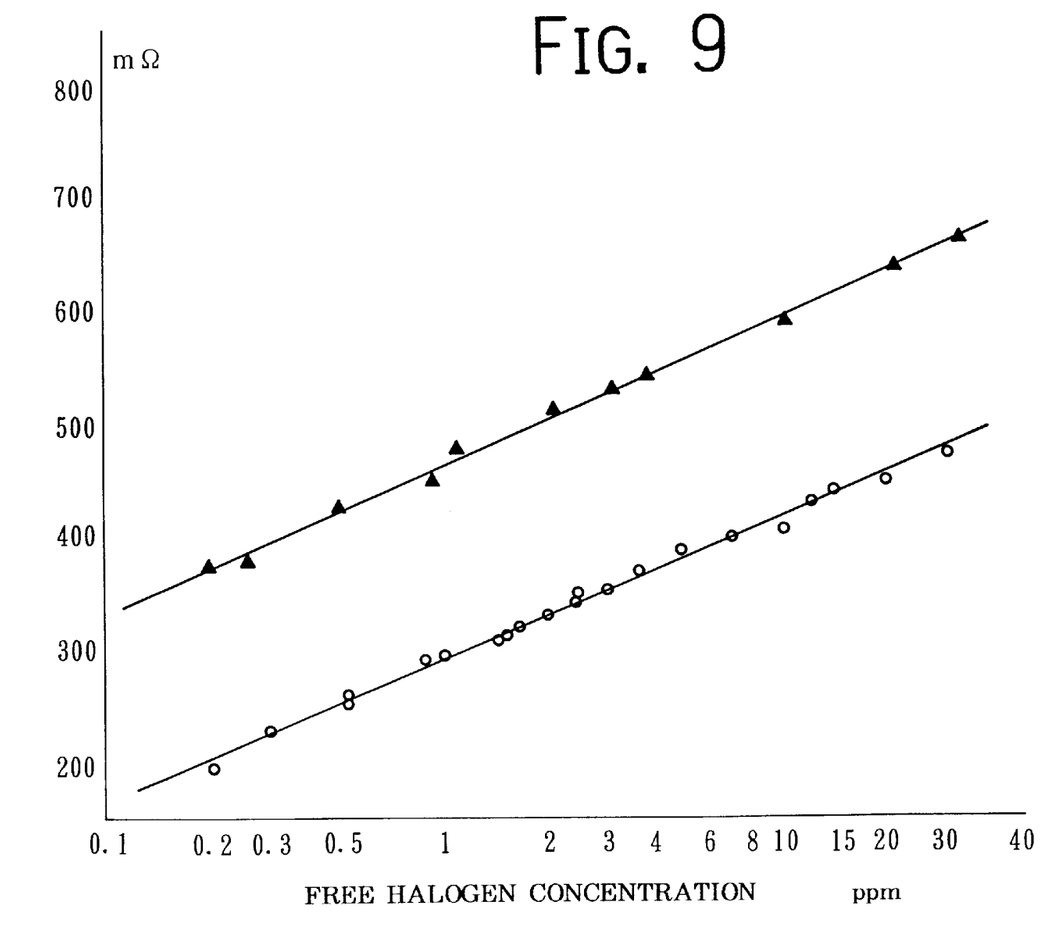
FIG. 9 is a graph on which the correlation between the free halogen concentration and the electric potential difference of Embodiment 1 is plotted.

As shown in the graph of FIG. 9, the results obtained from the above evaluation of the electrolyzed sodium bromide solution (NaBr solution) were plotted on a semi-logarithmic graph paper as indicated by symbols "○". This shows a clear linear relationship. In the same manner, on the semi-logarithmic graph paper of FIG. 9, the results of measurements obtained from the above evaluation of the electrolyzed salt water were plotted as indicated by symbols "▲". This shows a linear relationship with higher electric potential differences than the electrolyzed sodium bromide solution.

That is, there is a linear correlation between the actual free halogen concentration (logarithm) and the measured value of the electric potential difference. Additionally, both the electric potential difference (mV) and the converted free halogen concentration (ppm) may be indicated on the display section.

As described above, in both the water solution of sodium bromide and the salt water, the linear correlation was confirmed between the free halogen concentration (logarithm) and the electric potential difference. Therefore, the measured values of the electric potential difference are easily converted into the free halogen concentration; thus, it becomes possible to evaluate the free halogen concentration with high precision using a simple method during the treatment process of a sample liquid for evaluation.

Example 2

Measurements on the electric potential difference were carried out by using the same free halogen concentration evaluating device 9 (see FIG. 6) as Example 1 while the pH of the electrolyzed sample water was varied.

The adjustment of the pH of the electrolyzed sample water was carried out by using 1/10N of hydrochloric acid and 1/10N of sodium hydroxide. The concentration of the free halogen was measured by adding N,N'-diethylparaphenylenediamine reagent and using a photo-electric colorimetry analyzer (manufactured by HACH Co., Ltd.)—"DPD color analyzing method".

Electrolyzed sodium bromide solution having a concentration of 10 ppm was diluted so that the free bromide concentrations would be 1.3 ppm and 0.6 ppm respectively with the pH thereof being adjusted. Then, the aforementioned free halogen concentration evaluating device 9 was used so as to measure the electric potential difference. Next, salt water was adjusted in the same manner so that the free chlorine concentrations would be 1.3 ppm and 0.6 ppm respectively so as to measure the electric potential difference.

Figure 10:
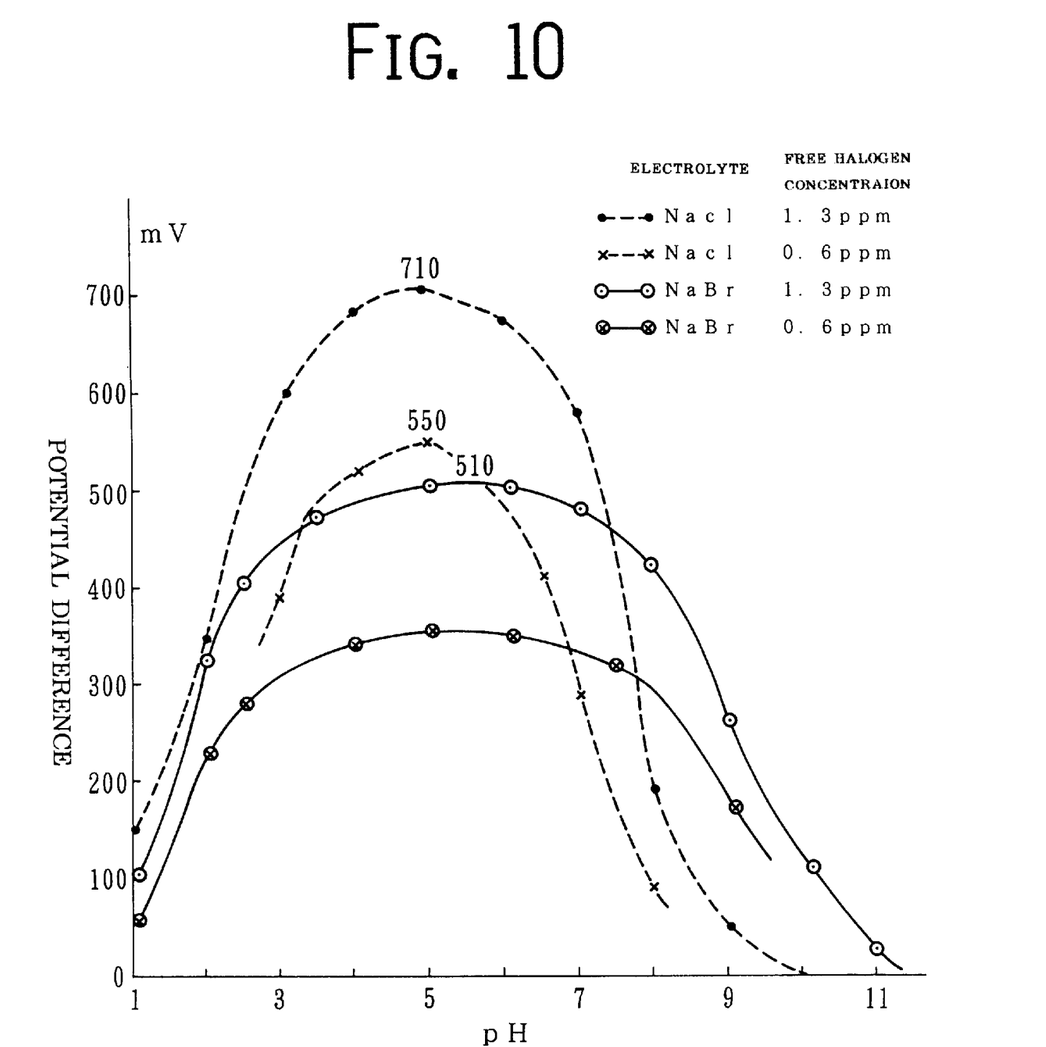
FIG. 10 is a graph showing the results of measurements carried out on the relationship between pH and the electric potential difference of Embodiment 2.

FIG. 10 shows the results of measurements of the relationship between the pH and the electric potential difference.

As shown in the graph of FIG. 10, at the same pH, salt water exhibits a higher electric potential difference than sodium bromide solution. This is the same as the case of FIG. 9 shown in Example 1. Here, in the case of salt water, the peak of the electric potential difference is at pH 5 and in the case of sodium bromide, the curve is more gentle near the peak and the peak is between pH 5 and pH 6, and in addition, the rise of the entire curve expands toward the higher region of pH.

Moreover, the following relationship can be confirmed from this graph. Assuming that the peak value at pH 5 of the electric potential difference of salt water is 100, conversions are respectively made as follows: The value at pH 6 is 95, that at pH 7 is 82, that at pH 8 is 27, that at pH 9 is 7, and that at pH 10 is 0. In the same manner, assuming that the peak value at pH 5 of the electric potential difference of sodium bromide solution is 100, conversions are respectively made as follows: The value at pH 6 is 100, that at pH 7 is 94, that at pH 8 is 82, that at pH 9 is 51 and that at pH 10 is 22.

Figure 11:
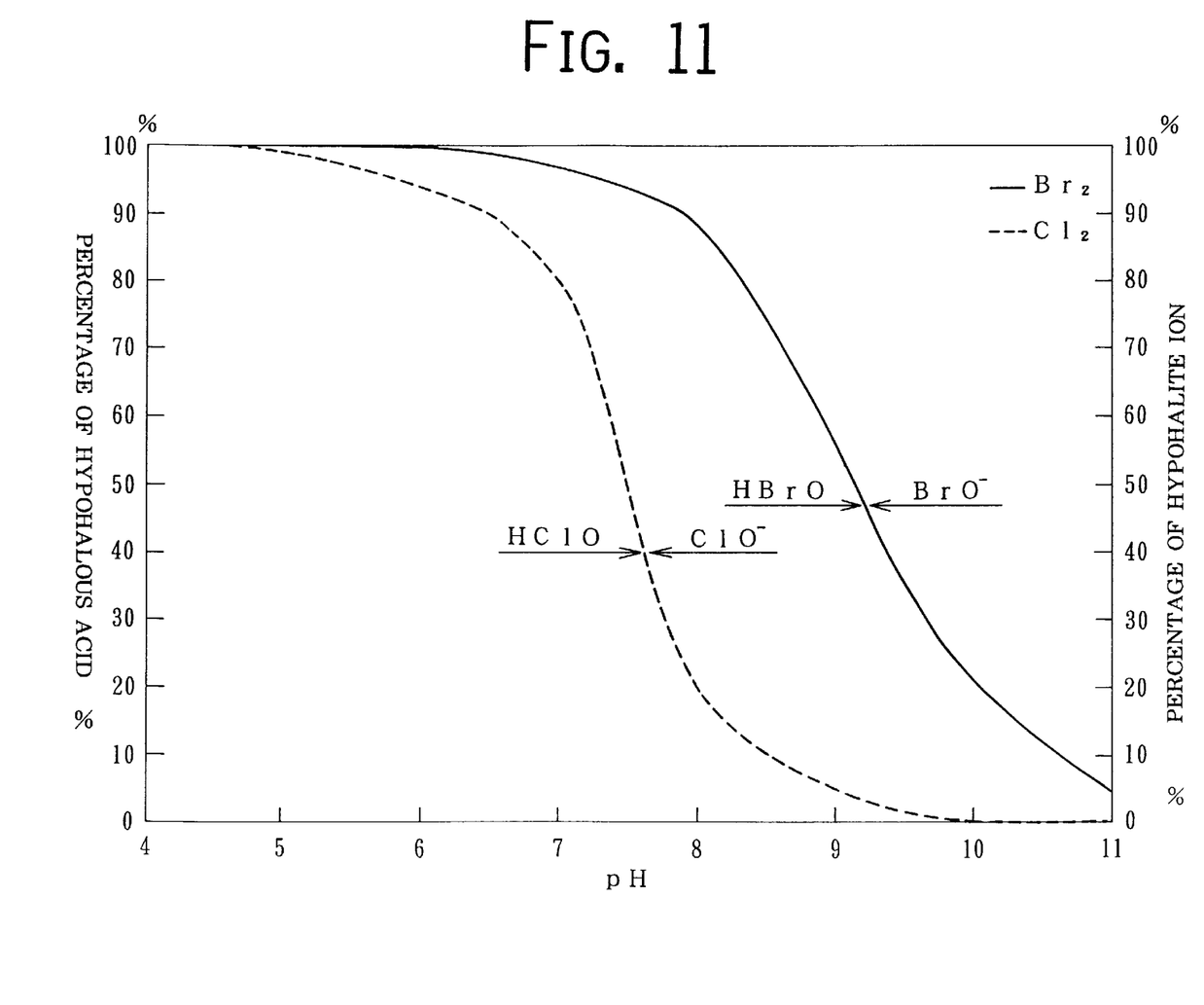
FIG. 11 is a graph showing the percentage (%) of existence of hypohalous acid and hypohalite ion.

The graph in FIG. 11 shows the percentage (%) of existence of hypohalous acid and hypohalite ion when bromine gas or chlorine gas dissolves into water and reacts so as to produce hypohalous acid as indicated by the following reaction formula [Bio Lab Co., Ltd. (United States)].

$$Br_2+H_2O \rightarrow HBrO+HBr, \quad Cl_2+H_2O \rightarrow HClO+HCl$$

As pH value becomes high, hypohalous acid is ionized to produce hypolialite ion as shown below:

$$HBrO+OH^- \rightarrow BrO^-+H_2O$$

$$HClO+OH^- \rightarrow ClO^-+H_2O$$

The respective pH conversion values, obtained by assuming that the peak value at pH 5 of the electric potential difference of salt water and sodium bromide solution is 100, are in fair accord with the percentage (%) of existence of hypohalous acid in the graph of FIG. 11. When the graph of FIG. 10 is observed by taking into consideration the percentage (%) of existence of hypohalous acid and hypohalite ion in the graph of FIG. 11, it can be confirmed that the free halogen concentration measured by the free halogen concentration evaluating device 9 of this Example is not in accord with the concentration of hypohalite ion ($ClO^-$), but closely in accord with the concentration of hypohalous acid (HClO).

Here, the DPD colorimetry analyzing method that is generally used shows the total ($ClO^-$+HClO) of the concentration of hypohalous acid (HClO) and the concentration of hypohalite ion ($ClO^-$) (it is mainly hypohalous acid that acts for the actual oxidative sterilization).

It is considered that the oxidative and sterilizing functions of electrolyzed sample water are high in a weak acidic region; and conventionally, there has not been an effective method for easily analyzing and measuring the concentration of hypohalous acid (HClO). For a comparatively simple and easy method, there has been a method to measure the concentration of hypohalous acid (HClO) by the difference between the free halogen concentration derived from the DPD color analyzing method ($ClO^{13}$+HClO) and the hypohalite ion ($ClO^-$) derived from the ion chlomatography.

Here, as compared with the above conventional method, the present example makes it possible to evaluate the concentration corresponding to hypohalous acid (HClO) with a very simple method and by only one measurement. Additionally, based upon the rate of existence with the pH at the time of measuring, the measured values may be converted to the free halogen concentration ($ClO^-$+HClO) of the DPD colorimetry analyzing method.

The present invention, which has the above-mentioned construction, provides the following effects;

Since it is difficult to lower the activity of the free halogen decomposing substance with time, it is possible to provide an evaluation method and an evaluation system of free halogen concentration which eliminate the necessity of early exchanging or recycling of the catalyst, as compared with a conventional method or system.

What is claimed is:

1. An evaluation method of free hypohalous acid concentration comprising:

forming a main flow path of a sample liquid for evaluation through which the sample liquid flows and a sub-region that communicates with said main flow path for trapping sample liquid therein, said sub-region having no outlet for said trapped sample liquid during evaluation of said free hypohalous acid concentration;

decomposing free hypohalous acid in the trapped sample liquid by a free hypohalous acid decomposing substance in said sub-region;

installing a potential-measuring electrode in said main path, while installing a reference electrode in said sub-region at a position where free hypohalous acid of the trapped sample liquid has been decomposed; and evaluating the free hypohalous acid concentration from the electric potential difference between said reference electrode and said potential-measuring electrode.

2. An evaluation system of free hypohalous acid concentration comprising:

a main flow path of a sample liquid for evaluation through which the sample liquid flows;

a sub-region that communicates with said main flow path for trapping sample liquid therein, said sub-region having no outlet for the trapped sample liquid during evaluation of said fee hypohalous acid concentration;

a potential-measuring electrode that is installed in said main flow path;

a free hypohalous acid decomposing substance which decomposes free hypohalous acid in the trapped sample liquid in said sub-region; and a reference electrode that is installed in the sub-region at a position where the free hypohalous acid in the trapped sample liquid has been decomposed; wherein the free hypohalous acid concentration is evaluated from the electric potential difference between said reference electrode and said potential-measuring electrode.

3. The evaluation system of free hypohalous acid concentration according to claim 2, wherein a catalyst is used as the free hypohalous acid decomposing substance.

4. The evaluation system of free hypohalous acid concentration according to claim 3, wherein the catalyst is one selected from the group consisting of activated carbon and an oxide of a metal selected from the group consisting of nickel, iron, cobalt, titanium and manganese.

5. The evaluation system of free hypohalous acid concentration according to claim 2, wherein an air-releasing means for discharging air and generated gases in the sub-region is provided.

6. The evaluation system of free hypohalous acid concentration according to claim 3, wherein an air-releasing means for discharging air and generated gases in the sub-region is provided.

7. The evaluation system of free hypohalous acid concentration according to claim 4, wherein an air-releasing means for discharging air and generated gases in the sub-region is provided.

* * * * *

UNITED STATES PATENT AND TRADEMARK OFFICE
CERTIFICATE OF CORRECTION

PATENT NO.    : 6,617,168 B1
DATED         : September 9, 2003
INVENTOR(S)   : Shinichi Nakamura et al.

It is certified that error appears in the above-identified patent and that said Letters Patent is hereby corrected as shown below:

Title page,
Item [75], Inventors, change "Shinichi Nakamura, Osaka (JP):
Kunihiko Fukutsuka, Nabikino (JP); Yasushi Hanano, Osaka (JP)," to
-- Shinichi Nakamura, Osaka (JP); Kunihiko Fukutsuka, Osaka (JP);
Yasushi Hanano, Osaka (JP) --

Signed and Sealed this

Twenty-first Day of June, 2005

JON W. DUDAS
*Director of the United States Patent and Trademark Office*